US006150167A

United States Patent [19]
Carpenter et al.

[11] Patent Number: 6,150,167
[45] Date of Patent: Nov. 21, 2000

[54] METHOD OF DETERMINING CONIFER EMBRYO MATURITY USING SUGAR ALCOHOL CONTENT

[75] Inventors: Carolyn V. Carpenter, Normandy Park; Martha K. Koester, Seattle, both of Wash.

[73] Assignee: Weyerhaeuser Company, Federal Way, Wash.

[21] Appl. No.: 09/253,169

[22] Filed: Feb. 19, 1999

Related U.S. Application Data

[60] Provisional application No. 60/075,164, Feb. 19, 1998.

[51] Int. Cl.$^7$ ..................................................... C12N 5/04
[52] U.S. Cl. .............................. 435/422; 435/4; 435/430; 435/430.1
[58] Field of Search ................................... 435/422, 430, 435/430.1, 4

[56] References Cited

U.S. PATENT DOCUMENTS

| | | |
|---|---|---|
| 5,036,007 | 7/1991 | Gupta et al. . |
| 5,413,930 | 5/1995 | Becwar et al. . |
| 5,464,769 | 11/1995 | Attree et al. . |
| 5,491,090 | 2/1996 | Handley et al. . |
| 5,506,136 | 4/1996 | Becwar et al. . |
| 5,677,185 | 10/1997 | Handley et al. . |
| 5,731,191 | 3/1998 | Rutter et al. . |
| 5,731,203 | 3/1998 | Handley et al. . |
| 5,731,204 | 3/1998 | Rutter et al. . |

OTHER PUBLICATIONS

Baron, Frank J. Metabolic patterns in dormant and germinating seeds of sugar pine (*Pinus lambertiana*, Dougl.). In *Advancing Frontiers of Plant Sciences*, Lo–kesh Chandra, ed., 24:47–63 (1970).
Bernabé, M., R. Fenwick, J. Frias, J. Jiménez–Barbero, K. Price, S. Valverde, and C. Vidal–Valverde. Determination, by NMR spectroscopy, of the structure of ciceritol, a pseudotrisaccharide isolated from lentils. *Journal of Agricultural and Food Chemistry* 41: 870–872 (1993).
Chien, C.–T., T.–P. Lin, C.–G. Jou, and G.–R. Her. Occurrence of a novel galactopinitol and its changes with other non–reducing sugars during development of *Leucaena leucocephala* seeds. *Plant Cell Physiology* 37: 539–544 (1996).
Górecki, R. J., A. I. Piotrowicz–Cieślak, L. B. Lahuta, and R. L. Obendorf. Soluble carbohydrates in desiccation tolerance of yellow lupin seeds during maturation and germination. *Seed Science Research* 7: 107–115 (1997).
Gupta, P. K. and D. J. Durzan. Biotechnology of somatic polyembryogenesis in plantlet regeneration in loblolly pine. *Bio/Technology* 5: 147–151 (1987).
Handley, L. W., L. W. Pharr, and R. F. McFeeters. Relationship between galactinol synthase activity and sugar compositions of leaves and seeds of several crop species. *Journal of the American Society of Horticultural Science* 108(4) 600–605 (1983).

Horbowicz, M., P. Brenac, and R. L. Obendorf. Fagopyritol B1, O–α–D–galactopyranosyl–(1→2)–D–*chiro*–inositol, a galactosyl cyclitol in maturing buck–wheat seeds associated with desiccation tolerance. *Planta* 205: 1–11 (1998).
Horbowicz, M. and R. L. Obendorf. Seed desiccation tolerance and stability: Dependence on flatulence producing oligosaccharides and cyclitols—review and survey. *Seed Science Research* 4: 358–405 (1994).
Horbowicz, M., R. L. Obendorf, B. D. McKersie, and D. R. Viands. Soluble saccharides and cyclitols in alfalfa (*Medicago sativa* L.) somatic embryos, leaflets, and mature seeds. *Plant Science* 109: 191–198 (1995).
Kuo, T. M. Isolation and Identification of galactinol from castor oilseed meal. *Journal of the American Oil Chemists Society* 69: 569–574 (1992).
Kuo, T. M., C. A. Lowell, and T. C. Nelsen. Occurrence of pinitol in developing soybean seed tissues. *Phytochemistry* 45: 29–35 (1997).
Murphy. J. B. and M. F. Hammer. Respiration and soluble sugar metabolism in sugar pine embryos. *Physiologia Plantarum* 74: 95–100 (1988).
Obendorf, R. L. Oligosaccharides and galactosyl cyclitols in seed desiccation tolerance. *Seed Science Research* 7: 63–74 (1997).
Obendorf, R. L., M. Horbowicz, A. M. Dickerman, P. Brenac, and M. E. Smith. Soluble oligosaccharides and galactosyl cyclitols in maturing soybean seeds *In planta* and In vitro, *Crop Science* 38: 78–84 (1998).
peterbauer, T. and A. Richter. Galactosylononitol and stachyose synthase in seeds of adzuki bean. *Plant Physiology* 117: 165–172 (1998).
Phillipy, Brian Q. Identification of inositol 1,3,4–triphosphate 5 kinase and inositol 1,3,4,5–tetrakisphosphate 6–kinase in immature soybean seeds. *Plant physiology* 116: 291–297 (1998).
Teasdale, R. D., P. A. Dawson, and H. W. Woolhouse. Mineral nutrient requirements of loblolly pine. (*Pinus taeda* cell suspension culture). *Plant physiology* 82: 942–945 (1986).

*Primary Examiner*—Leon B. Lankford, Jr.

[57] ABSTRACT

The invention relates to the knowledge of sugar alcohols as indicators of biochemical maturity of pine zygotic and somatic embryos. It has been discovered that loblolly pine zygotic embryos have a progression of different sugar alcohols as they approach biochemical maturity. Pinitol is the first sugar alcohol to appear in abundance. This is followed by D-chiro-inositol, and finally by fagopyritol B1. As a later appearing alcohol becomes more abundant in the embryos, the earlier ones decrease in amount present. Analysis of the embryo sugar alcohols can be helpful in determining when to harvest cones from seed orchards. Further it can be used as a guideline for formulation of more effective culture media in the propagation of somatic embryos by tissue culture. There appears to be a requirement for fagopyritol B1 if good germination of somatic embryos is to be achieved.

5 Claims, No Drawings

METHOD OF DETERMINING CONIFER EMBRYO MATURITY USING SUGAR ALCOHOL CONTENT

This application claims priority from provisional application Ser. No. 60/075,164, filed Feb. 19, 1998.

The present invention is directed to a method of determining biochemical maturity and readiness for harvest and subsequent germination of conifer embryos. The method is especially useful for the southern pine species and is applicable to determining both the optimum time of harvest for cones and the developmental maturity of somatic embryos produced by tissue culture.

BACKGROUND OF THE INVENTION

Most reforestation is now done using seedlings grown in nurseries, if the Douglas-fir region of the Pacific Northwest or southern pine region of the Southeastern United States may be taken as examples. Most seed for the nurseries is provided by seed orchards that, in some cases, are now a third generation of selected trees. Most of this orchard produced seed has been open pollinated and much of the pollen comes from wild trees located outside the orchard. For this reason, the maximum genetic gain has not been reached. Some full sib seed is produced, in which both cone and pollen parents are known. However, this is in far too short supply and is much too expensive for any but very specialized applications. Some is effectively bulked up as nursery stock used for the production of rooted cuttings. While still in the early stages of commercial production of reforestation stock, selected seed may also be bulked up by tissue culture methods.

The optimum time to harvest cones for their contained seeds has always been a problem in forest tree nurseries. Too early harvest will yield immature seed that may have poor germination or result in trees having less than the desired vigor. Too late harvest may result in significant seed loss from cones opening. In analogous fashion, it is always problematical when somatic embryos have obtained the maturity that will lead to good germination.

In seeds naturally grown on plants, "maturity" corresponds to the time when the seed dries and dehisces from the mother plant. This point in time may be assumed to represent the seed (zygotic) embryo biochemical maturity as well as morphological maturity. Morphological maturity may be defined as the time when cell division in the embryo ceases. Biochemical maturity is seen as the time when accumulation of storage products is complete and the seed is ready to enter dormancy. Essentially, the genetically pre-programmed development and environmental responses of the embryo and mother plant dictate maturity. It is only necessary to harvest the mature seed at the proper time and treat it optimally after harvest. However, this is not the case with somatic embryos. Scientists must dictate the timing and protocol of every shift in hormones, media composition, water potential, photoperiod, and temperature. In somatic embryos, there is no period of quiescence which clearly demarcates maturation from readiness for germination in natural seed.

Tissue culture of somatic embryos of coniferous species has received heavy emphasis in recent years as a means of supplying genetically superior reforestation stock. A seed, or the contained embryo, is placed on a culture medium with appropriate mineral, vitamin and hormone nutrients. When initiation is successful, a gelatinous mass will form containing a multiplicity of immature embryos genetically identical to the parent embryo. This mass is then transferred to another medium, often reduced in hormone content, for maintenance and multiplication of the embryos. The culture, or a portion of it, is again transferred to a growth or development medium where the embryos mature to a point where they morphologically resemble natural zygotic embryos. These embryos may then be placed on a germination medium where the resulting plantlets are allowed to grow until they can be transferred to soil. Alternatively the embryos can be placed in manufactured seeds and be planted directly in soil. U.S. Pat. No. 5.036,007 to Gupta et al. is exemplary of the tissue culture methods used for coniferous species.

Unfortunately, tissue culture is known to be a highly unpredictable science. It is well accepted that there is a high level of unpredictability between and even within genera in morphological and biochemical development. This is particularly true comparing the angiosperms and gymnosperms. It has been shown many times that what might be true for alfalfa or soy beans is not necessarily true at all for pine or Douglas-fir trees. This applies even below the species level. A culturing protocol that works well for one genotype may not be optimum for another genotype obtained from the same cone.

Appearance has heretofore been used as a criterion of maturity for somatic embryos produced by tissue culture; i.e., if a somatic embryo looked like a mature zygotic embryo it was presumed to be mature. Unfortunately, this crude tool has proved to be highly undependable. The level of "storage products" has also received some attention as a maturity indicator. Storage products are generally defined as the protein, lipid, and carbohydrate materials needed to support the embryo during and immediately after germination. One group of workers has found that inducing an exaggerated level of triacylglycerides in conifer somatic embryos improves germination (Attree et al., U.S. Pat. No. 5,464,769).

For many angiosperm species at least, it is now known that embryo biochemical maturity lags behind morphological maturity by a significant period of time. It is during this time interval, between morphological and biochemical maturity, that oligosaccharides of the raffinose series develop. As examples, Górecki et al. (1997) and Obendorf (1997) discuss the importance of the oligosaccharides and note that certain cyclitols and galactosyl cyclitols appear to be formed in the time period between morphological and biochemical maturity. The presence of a protein group called dehydrins, generally formed after accumulation of storage products is complete, is also an indicator of angiosperm readiness to germinate. Published application WO 98/48279, commonly assigned with the present one, describes a method of estimating maturity of conifer somatic embryos by analysis of their oligosaccharides. This application is herein incorporated in its entirety by reference.

Conifer seed, whether full sib seed from nurseries or seed gathered in the wild, will have all of the genetic diversity of the parent trees. Some seeds will produce trees with more desirable characteristics than other seeds taken from the same cone. Tissue culture offers a way to select the best trees before major plantings have been made in the forest. Embryos at the maintenance phase may be frozen in liquid nitrogen and stored while a small sample of the clone is further cultured and outplanted. After three to five years the characteristics of the clone are readily apparent and the decision can then be made whether or not to remove the remainder of the embryos from cryogenic storage for larger scale propagation.

The requirements of an embryo during maturation are completely different and virtually opposite to the requirements of an embryo during germination. In early and mid development, morphology is the outcome or result of changes that have taken place at the biochemical level. However, it does not reveal all of them, particularly at the critical juncture between biochemical maturity and readiness to germinate. More precise biochemical tools to signal these changes would be extremely helpful to seed orchardists and to the scientists working with somatic embryogenesis. In the case of the latter group, the availability of such tools would be of great value, both for determining readiness for germination and for developing culture medium protocols to optimally achieve such readiness. It would allow them to identify and develop needed protocol changes and the timing of their imposition.

The literature on the biochemistry of the late development period in small seed crops has noted the presence of sugar alcohols and presumed that they serve in the acquisition of desiccation tolerance. In the discussion that follows, literature citations list only the lead author and date of publication. Full citations are given in the attached bibliography at the end of the specification.

Horbowicz et al. (1998) characterized a major soluble carbohydrate in buckwheat as O-α-D-galactopyranosyl-(1→2)-D-chiro-inositol or fagopyritol B1. They suggest that accumulation of fagopyritol was associated with acquisition of desiccation tolerance during the latter part of seed development. D-chiro-inositol and myo-inositol were present throughout seed development but pinitol or other O-methylated inositols were not found at any time.

Obendorf et al. (1998) note that fagopyritol and galacto-pinitol accumulate in soybean axis tissues in parallel with stachyose accumulation, in association with the advent of desiccation tolerance. Phillipy (1998) notes various inositol derivatives in immature soybean tissue but does not discuss these in the context of embryo maturation. Peterbauer et al. (1998) note the synthesis of a galactosylcyclitol by stachyose synthase extracted from adzuki bean. Additionally, the enzyme catalyzed the galactinol-dependent synthesis of galactosylononitol from D-ononitol. Murphy et al. (1998), in an analysis of the soluble sugars and hydrolytic enzymes in sugar pine embryos before and during germination, made no note of any sugar alcohols other than pinitol, which was present at a constant low level throughout their seed incubation period. Kuo et al. (1997) identified pinitol as a major cyclitol in developing soybean. Pinitol was seen to decrease sharply as raffinose polysaccharides accumulated. Górecki et al. (1997) investigated cyclitols in lupine seeds during their period of maturation. They found D-pinitol, D-chiro-inositol, and myo-inositol, to be predominant in the early stages of seed growth. During maturation raffinose family oligosaccharides accumulated as did the galactosyl cyclitols; e.g., fagopyritols and galactopinitols. The increase of these latter compounds appeared to correlate with seed germinability after desiccation.

Chien et al. (1996) identified a galactopinitol in the late development stages of the seeds of leucaena seeds. Leucaena is a small leguminous tree and appears to be the only tree seed which has been investigated for cyclitols. Interestingly, the galactopinitol they found decreased during maturation while stachyose concentration increased. Horbowicz et al. (1995) looked at the maturation of alfalfa seeds and somatic embryos. They note that during maturation and desiccation of somatic embryos, changes in soluble carbohydrates are similar to those of seeds, with the notable exception of the lack of pinitol and galactosyl pinitols in the somatic embryos. Horbowicz et al. (1994) studied carbohydrates in the axes, cotyledons, embryos, and seeds of 19 species in 7 families in regard to desiccation tolerance. Considerable differences were found. Legumes tended to accumulate stachyose series oligosaccharides whereas many other species accumulated galactosyl derivatives of cyclitols. One species (castor bean) accumulated galactinol whereas buckwheat accumulated galacto-chiro-inositol (fagopyritol). The authors proposed that galactinol and galacto-chiro-inositol functioned in the same manner as raffinose in giving desiccation tolerance. The paper is a handy reference to the chemical structures of the various cyclitols.

Bernabé et al. (1993) detail a method used to identify the structure of ciceritol, a pseudotrisaccharide found in lentils. Kuo (1992) noted that galactinol (1-O-α-D-galactopyranosyl-D-myo-inositol) is thought to be an essential intermediate in the biosynthesis of the raffinose series polysaccharides in plant tissues. This paper describes a method for extracting reference quantities of galactinol from castor oilseed meal. Baron (1970) studied the germination of sugar pine seeds. This early paper noted that during stratification, fat content decreased as did raffinose and stachyose. These oligosaccharides completely disappeared during germination. The only cyclitol examined was myo-inositol which was found to increase as germination progressed.

Thus, it is seen that the literature regarding the biochemistry of the late development period has been essentially silent as to the presence and presumed function of the sugar alcohols in conifer seeds and/or embryos.

SUMMARY OF THE INVENTION

The present invention is a method for determining biochemical maturity of embryos of plants within the botanical order Coniferales. It is particularly pertinent to embryos of trees within the genus Pinus and most especially pertinent to the four species and their inter-hybrids known as the southern yellow pines. The method is based on determination of simple or complex cyclic sugar alcohols or cyclitols (polyhydroxy cyclohexanes and their derivatives) in conifer embryos. This may be done using the techniques of high pressure liquid chromatography and gas chromatography. It has been determined for zygotic embryos of loblolly pine (*Pinus taeda* L.), Douglas-fir (*Pseudotsuga menziesii* (Mirb.) Franco), and white spruce (*Picea glauca* (Moench.) Voss) that these cyclitols are formed during mid development as well as in the time period between morphological maturity and biochemical maturity. The belief is that the cyclitols act in concert with certain oligosaccharides developed late in the maturation process to provide desiccation protection to the embryos. It is possible that in some cases they may be essential for germination. One would by analogy expect the same cyclitols to be critically important in somatic embryos to assure normal germination and this appears to be the case.

It has been found in loblolly pine (*Pinus taeda* L.) that three sugar alcohols are particularly important. These have been found to form a progression in abundance as maturation occurs. Pinitol is initially present in the early stages of maturation. Later, D-chiro-inositol becomes the prominent alcohol. As biochemical maturity is closely approached, D-chiro-inositol decreases and fagopyritol B1 appears for the first time in significant quantity. Fagopyritol ultimately becomes the dominant sugar alcohol. The knowledge of this progression is a useful tool for estimating biochemical maturity of embryos.

It has been found that oligosaccharides of the raffinose series are also important markers of maturity. However, unlike the sugar alcohols these oligosaccharides appear quite abruptly at biochemical maturity and do not appear during early or mid development. For this reason, the sugar alcohols are more informative of the embryo development over time leading to biochemical maturity.

The present invention is further directed to conifer somatic embryos containing detectable and significant amounts of selected cyclitols.

It is an object of the invention to provide a method for determining biochemical maturity of conifer embryos It is yet an object to provide a method that may be used as a guide for determining cone harvest times.

It is a further object to provide a method that may be used to determine biochemical maturity of somatic embryos.

It is also an object to provide biochemically mature somatic embryos that are ready for germination.

These and many other objects will become readily apparent upon reading the following detailed description.

DETAILED DESCRIPTION OF THE PREFERRED EMBODIMENTS

Analysis of the samples was carried out using the following procedures. Extracts of mature seeds of loblolly pine were examined by a high pressure liquid chromatographic (HPLC) technique known as anion exchange chromatography and described as follows. Where specific suppliers are noted this should not be considered an endorsement of their products since equally suitable products may be available from other vendors.

The column used for determining sugar alcohols was the Dionex CarboPac MA-1 (P/N 44066) (Dionex Corp., Sunnyvale Calif.). This is a 4×250 mm 7.5 $\mu$m particle size column with 15% crosslinking of a latex substrate functionalized with an alkyl quaternary ammonium group. The guard column (P/N 44067) of the same material is 4×50 mm. A Dionex MFC-1 iminodiacetate functionalized column to remove metal ions was in line before the guard column and the linked set is treated as a single unit. A Dionex anion trap column ATC-1, 9×24 mm was installed before the Waters U6K manual injector (Waters Corp., Milford Mass.) to remove carbonate before injection.

Sugar alcohols were eluted with a gradient system of two Waters 510 pumps controlled by the Waters Millenium chromatography system version 2.15. Post column addition of NaOH was done with a Scientific Systems, Inc., State College Pa., Model 350 self flushing pump with an internal mixing column. The 510A pump uses 100% ultrapure water. Solvent addition (SSI) NaOH and 510B NaOH were 500 mmolal. Solvents were degassed and sparged with helium. Water was weighed and sparged for at least 20 minutes to minimize possible exposure of the NaOH solution to $CO_2$.

The flow rate was 0.4 mL/min for the 510 gradient system and the SSI pump. The gradient was as follows:

TABLE 1

| Step | Time, min | % A ($H_2O$) | % B (500 mM NaOH) | Curve Form |
| --- | --- | --- | --- | --- |
| 1 | 0 | 95 | 5 | Initial |
| 2 | 8 | 95 | 5 | Initial |
| 3 | 23 | 0 | 100 | Linear |
| 4 | 37 | 0 | 100 | Step |
| 5 | 40 | 95 | 5 | Linear |
| 6 | 75 | 95 | 5 | Step |

The detector was a Waters Pulsed Amperometric Detector with a gold working electrode and a base-resistant reference electrode. Pulse time settings were $T_1=0.216$ sec, $T_2=0.216$ sec, and $T_3=0.299$ sec. The voltage $E_1$ was determined daily by a volt ammogram scan of $\mu$amps vs mvolts over a range of +700 mV to −700 mV. It from 120 to 150 mV. The other two voltages are calculated from $E_1$, where $E_2=650$ mV, and $E_3=E_1-650$ mV. Data were collected at the 10 $\mu$amp scale for analytical work and at 50 or 100 $\mu$amp for preparative work.

Sugar alcohol stock solutions used as standards for preparative work were 25 mM. Working standards were prepared at 250 $\mu$M, 83.33 $\mu$M and 25 $\mu$M. For both standards and samples 50 $\mu$L was injected with a syringe made for use with the Waters U6K manual injector. Average retention times are listed below. Quantitation is by area except for pinitol and myo-inositol which are quantitated by height because of the close elution time.

TABLE 2

MA-1 Retention Times

| Component | Retention Time, min |
| --- | --- |
| D-pinitol | 13.6 |
| myo-inositol | 14.7 |
| scyllo-inositol | 16.2 |
| D-chiro-inositol | 22.6 |
| L-chiro-inositol | 22.6 |
| epi-inositol | 22.8 |
| allo-inositol | 39.5 |
| fagopyritol B1 | 40.2 |
| muco-inositol | 44.6 |
| glycerol | 13.0 |
| galactinol | 22.8 |
| sorbitol | 33.6 |
| dulcitol | 34.0 |

Preparative chromatography was preformed when individual peaks were isolated for further analysis. Pooled fractions were desalted with a mixed bed ion exchange resin. Desalted volume was reduced to near dryness under vacuum and transferred to vials for further analysis by nuclear magnetic resonance (NMR), or hydrolysis and reanalysis of the breakdown products by HPLC.

No standard for fagopyritol B1 was available from the usual sources. Therefore, a standard was prepared from buckwheat seeds (e.g., see Horbowicz et al. 1998). The seeds still retaining their seed coat were ground and extracted with 80% ethanol. The extract was subjected to HPLC and the material eluting as a 40.2 minute peak was subjected to NMR for confirmation of structure. An aliquot of the sample was enzymatically hydrolyzed with α-galactosidase and the product again analyzed by HPLC. The 40.2 minute peak had disappeared and new peaks representing D-galactose and D-chiro-inositol were present, further confirming structure of the reference sample.

Fagopyritol B1 from the HPLC chromatogram of pine embryos was positively identified as follows. A 1.75 N solution of trifluoroacetic acid was prepared. The HPLC fraction was reduced to dryness under vacuum and taken up in 2 mL of $H_2O$. A 1 mL portion was removed for NMR, 50 $\mu$L of which was analyzed by HPLC as a control. The other 1 mL was dried under a stream of nitrogen at 70° C. A 1 mL aliquot of trifluoroacetic acid solution was added to the dried sample and vortexed. It was then hydrolyzed at 70° C. After hydrolysis the material was again dried under nitrogen and 1 mL water added. The resulting sample was analyzed by HPLC. The fagopyritol B1 peak had been replaced by peaks representing galactose and D-chiro-inositol.

As a confirmatory analysis, 100 $\mu$L of deionized concentrated putative fagopyritol B1 fractions were incubated with 200 $\mu$L of dialyzed α-galactosidase over-night in a water bath maintained at 37° C. All samples were adjusted to a final volume of 1 mL and analyzed by HPLC. Again, the fagopyritol B1 peak had disappeared and peaks representing galactose and D-chiro-inositol were prominent. To ascertain activity of the enzyme a 5 mM stock solution of galactinol and 25 μL from buckwheat samples were treated in the same manner. Additional confirmation of the structure was made by nuclear magnetic resonsnce.

LOBLOLLY PINE CULTURE

The following schedule of treatments has been very successfully used for the growth of plantlets by somatic embryogenesis of loblolly pine (*Pinus taeda* L.). Explants were the female gametophytes containing the zygotic embryos which had been removed from seeds 4 to 5 weeks after fertilization. The seed coat was removed but the embryo was not further dissected out of the surrounding gametophyte other than to excise the nucellar end. Seeds were obtained from cones supplied by a Weyerhaeuser Company seed orchard located at Washington, N.C. The cones were stored at 4° C. until used. Immediately before removal of the immature embryos the seeds were sterilized using an initial washing and detergent treatment followed by a 10 minute sterilization in 15% $H_2O_2$. The explants were thoroughly washed with sterile distilled water after each treatment. Tables 3 and 4 give media compositions for loblolly pine embryogenesis.

TABLE 3

*Pinus taeda* Basal Medium (Modified ½ P6 Basal Salts*)

| Constituent | Concentration, mg/L |
|---|---|
| $NH_4NO_3$ | 150.0 |
| $KNO_3$ | 909.9 |
| $KH_2PO_4$ | 136.1 |
| $Ca(NO_3)_2.4H_2O$ | 236.2 |
| $CaCl_2.4H_2O$ | 50.0 |
| $MgSO_4.7H_2O$ | 246.5 |
| $Mg(NO_3)_2.6H_2O$ | 256.5 |
| $MgCl_2.6H_2O$ | 50.0 |
| KI | 4.15 |
| $H_3BO_3$ | 15.5 |
| $MnSO_4.H_2O$ | 10.5 |
| $ZnSO_4.7H_2O$ | 14.4 |
| $NaMoO_4.2H_2O$ | 0.125 |
| $CuSO_4.5H_2O$ | 0.125 |
| $CoCl_2.6H_2O$ | 0.125 |
| $FeSO_4.7H_2O$ | 13.9 |
| $Na_2EDTA$ | 18.65 |
| Maltose | 20,000.–30,000. |
| myo-Inositol | 100. |
| Casamino acids | 500. |
| L-Glutamine | 1000. |
| Thiamine.HCl | 1.00 |
| Pyridoxine.HCl | 0.50 |
| Nicotinic acid | 0.50 |
| Glycine | 2.00 |
| Gelrite+ | 200. |
| pH adjusted to 5.7 | |

*According to Teasdale, Dawson, and Woolhouse (1986) as modified
+Used if a solid medium is desired

TABLE 4

Composition of Media for Different Stage Treatments $BM_1$ -- Induction Medium
BM + 2,4-dichlorophenoxyacetic acid (2,4-D) (15 μM) + kinetin (KIN) (2 μM) + N6-benzylaminopurine (BAP) (2 μM)
$BM_2$ -- Maintenance and Multiplication Medium
BM + 2,4-D (5 μM) + KIN (0.5 μM) + BAP (0.5 μM) + 4900 mg/L additional myo-inositol. Gelrite is added when a solid medium is desired.
$BM_3$ -- Cotyledonary Embryo Development Medium TABLE 4-continued Composition of Media for Different Stage Treatments BM + 50–100 mg/L abscisic acid (ABA) + 18% PEG-4000 & 8000 mixture + 2–2.5% maltose + 900 mg/L additional myo-inositol + 1000 mg/L glutamine + 0.125% activated charcoal. No gellant. The following amino acid mixture is added: L-proline - 100 mg/L, L-asparagine - 100 mg/L, L-arginine - 50 mg/L, L-alanine 20 mg/L, and L-serine - 20 mg/L.
$BM_4$ -- Germination Medium
BM modified by replacing maltose with sucrose at 20,000 mg/L, myo-inositol to 100.0 mg/L, glutamine and casamino acids are omitted + 0.2% Gelrite and 0.25% activated charcoal.

Stage I—Induction Sterile gametophytes with intact embryos were placed on a solid BM1 culture medium and held in an environment at 22°–25° C. with a 24 hour dark photoperiod for a time of 3–5 weeks. The length of time depended on the particular genotype being cultured. At the end of this time a white mucilagenous mass had formed in association with the original explants. This appears to be identical with that described by Gupta and Durzan (1987). Microscopic examination revealed numerous early stage embryos associated with the mass. These are generally characterized as having a long thin walled suspensor associated with a small head with dense cytoplasm and large nuclei. Osmolality of the induction medium may in some instances be as high as 170 mM/kg. Normally it will be about 160 mM/kg or even lower. The osmolality of the medium described above was 150 mM/kg.

Stage II—Maintenance and Multiplication Early stage embryos removed from the masses generated in the induction stage were first placed on a $BM^2$ gelled maintenance and multiplication medium. This differs from the induction medium in that the growth hormones (both auxins and cytokinins) were reduced by at least a full order of magnitude. Osmolality of this medium will typically be raised from that of the induction medium to about 180 mM/kg or higher by increasing the concentration of myo-inositol to 0.5% w/v. The temperature and photoperiod were again 22°–25° C. with 24 hours in the dark. Embryos were cultured for 12–14 days on $BM_2$ solid medium before transferring to a liquid medium for further subculturing. This liquid medium was of similar composition but lacked the gellant. The embryos at the end of the solid maintenance stage were similar in appearance to those from Stage I. After 5 to 6 weekly subcultures on the liquid maintenance medium advanced early stage embryos had formed. These are characterized by smooth embryonal heads estimated to have over 100 individual cells with multiple suspensors.

Osmotic potential of the maintenance media should typically fall within the range of about 180–400 mM/kg for *Pinus taeda*. Most typically the maintenance media should be in the neighborhood of about 1.5 times higher in osmotic potential than the induction or multiplication media. As was noted earlier, the requirements for elevation of osmotic potential at this stage will vary for different species and may vary somewhat for differing genotypes within a given species.

Stage III—Embryo Development The advanced early stage embryos from Stage II culture were transferred to a filter paper support placed on a pad saturated with liquid development medium. This medium either lacks growth hormones entirely or has them present only at very low levels. However, here abscisic acid (5-(1-hydroxy-2,6,6-trimethyl-4-oxo-2-cyclohexen-1-yl)-3-methyl-2,4-pentadienoic acid) (ABA) may be a necessary material for further development. As was noted earlier, the inclusion of an adsorbent material in this medium is highly advantageous. The adsorbent may be chosen from a number of chemical materials having extremely high surface area and/or controlled pore size such as activated charcoal, soluble and insoluble forms of poly(vinyl pyrrolidone), activated alumina, silica gel, molecular sieves, etc. The adsorbent will normally be present in a concentration of about 0.1–5 g/L, more generally about 0.25–2.5 g/L. Development time is generally 8–14 weeks in the dark. At the end of this period the cotyledonary embryos are 2–3 mm long and closely resemble mature zygotic embryos in morphology.

Stage IV—Drying The embryos still on their filter paper support are lifted from the pad and placed in a closed container over a saturated solution of $K_2SO_4$, at a relative humidity of 97%, for a period of three weeks.

Stage V—Germination The dried cotyledonary embryos from Stage IV were rehydrated by placing them, while still on the filter paper support, for about 24 hours on a pad saturated with liquid germination medium. The embryos were then placed individually on solid $BM_4$ medium for germination. This is a basal medium lacking growth hormones which has been modified by substituting sucrose for maltose and eliminating organic nitrogen. After about 6–8 weeks under environmental conditions of 23–25° C. and a 16 hour light–8 hour dark photoperiod, the resulting plantlets were approximately 20 mm in length and had a well developed radicle and hypocotyl and green cotyledonary structure and epicotyl. Alternatively, the cotyledonary embryos may be made into artificial seeds.

Because of the reduced carbohydrate concentration, the osmotic potential of the germination medium is further reduced below that of the development medium. It will normally be below about 150 mM/kg and was, in the present example, about 100 mM/kg.

Stage VI—Conversion Plantlets from Stage V were removed from the germination medium and planted in a soil composed of equal parts of peat and fine perlite. Rooting percentage was excellent and the resulting plants showed good growth and vigor.

EXAMPLE 1

Determination of Biochemical Maturity in Loblolly Pine

Loblolly pine cones were picked from a seed orchard in Arkansas on August 20, October 3, and October 17. The last date was believed by conventional criteria to represent full biochemical maturity of the cones and was during the time of cone harvest time for seed. Cones were immediately packed in an iced cooler for transport to the laboratory. Within 24 hours the cones had been opened, the seeds removed, and embryos dissected from the seeds. The embryos were immediately frozen in liquid nitrogen until they could be analyzed.

Embryos were then extracted for determination of sugar alcohols by the method described earlier. Extraction was generally by the method described by Handley et al. (1983) using 80% ethanol. Briefly, the method involves grinding the embryos in 80% ethanol and heating at 70° C. for 10 minutes. The sample was centrifuged and the supernatant reserved. The solids remaining were resuspended in 80% ethanol and frozen at −10° C. for at least 30 minutes to ensure that all cell membranes had been ruptured. The tissue was again reground, heated, and centrifuged as before and the supernatant combined with that obtained earlier. To the pooled supernatants was added 5 µL of $^{14}$C glucose ($2.2 \times 10^6$ dpm). Duplicate 10 µL samples were counted in a scintillation counter. The remaining supernatant was evaporated to dryness under vacuum at 35–40° C. After cooling, the dried sample was washed with several mL of ethyl ether to remove lipids and color bodies. The sample was then dissolved in 0.5–1.0 mL of ultrapure water. A duplicate 10 µL sample was again counted for radioactivity. The sample was then used for HPLC separation of the sugar alcohols. Results of the determinations are given in Table 5 which follows.

TABLE 5

Sugar Alcohols in Loblolly Pine Zygotic Embryos

| Harvest Date | August 20 | October 3 | October 17 |
|---|---|---|---|
| Pinitol, nM/embryo | 65.9 | 9.1 | 3.8 |
| Pinitol, nM/mg* dry weight | 73.4 | 5.3 | 2.0 |
| Myo-inositol, nM/embryo | 21.4 | 10.1 | 5.7 |
| Myo-inositol, nM/mg dry weight | 23.9 | 5.9 | 3.0 |
| D-chiro-inositol, nM/embryo | 18.6 | 53.0 | 30.0 |
| D-chiro-inositol, nM/mg dry weight | 20.7 | 31.1 | 16.2 |
| Fagopyritol B1, nM/embryo | 0.8 | 20.4 | 38.9 |
| Fagopyyritol B1, nM/mg dry weight | 0.9 | 12.0 | 21.0 |

*nanomoles per milligram

At the initial harvest date of August 20 the seed embryos had attained full morphological maturity. They did not change in morphology for the duration of the sampling period. However, it is immediately evident that they underwent major biochemical changes in the almost two months between the initial and final harvests. In August only a trace amount of fagopyritol B1 was present. Pinitol was the predominant alcohol with myo-inositol and D-chiro-inositol in significant and about equal amounts. By early October pinitol had dropped to a relatively low level and myo-inositol had dropped to about 40% of the August value. However, D-chiro-inositol had peaked sharply and B1-fagopyritol was present in a significant amount. At the latter October date, just before seed drop, pinitol and myo-inositol had fallen to low levels, D-chiro-inositol had dropped to about half of its value two weeks earlier and B1-fagopyritol had doubled in amount.

It is evident from the above data that development of seed maturity can be closely followed and predicted by sugar alcohol analysis even though there is no visible change in embryo morphology.

EXAMPLE 2

Effect of Differing Culture Media on Loblolly Pine Somatic Embryo Sugar Alcohols Loblolly pine somatic embryos were cultured as described earlier in the tissue culture procedure. However one sample was obtained from embryos cultured in a development medium containing 50 mg/L abscisic acid (ABA) and another from embryos in a development medium containing 10 mg/L ABA and 7.5 mg/L giberellic acid ($GA_{4/7}$). The embryos were removed directly from the development medium and analyzed as before for sugar alcohols. Results are seen in following Table 6.

TABLE 6

Sugar Alcohols in Loblolly Pine Somatic Embryos

| Genotype | 7 | 7 | 5 | 5 |
|---|---|---|---|---|
| Culture Medium | ABA | ABA/GA$_{4/7}$ | ABA | ABA/GA$_{4/7}$ |
| Pinitol, nM/embryo | Negligible | Negligible | Negligible | Negligible |
| Myo-inositol, nM/embryo | 3.0 | 12.0 | 5.1 | 7.4 |
| Myo-inositol, nM/mg dry weight | 18.3 | 56.8 | 26.0 | 32.0 |
| D-chiro-inositol, nM/embryo | 23.3 | 61.6 | 24.1 | 29.2 |
| D-chiro-inositol, nM/mg dry wt. | 143.8 | 271.3 | 122.0 | 127.0 |
| Fagopyritol B1, nM/embryo | Trace (?) | Trace (?) | Trace (?) | Trace (?) |

The above results on pooled samples of 40 embryos in the case of genotype 7 and 10 for genotype 5 show that determination of the sugar alcohol types and levels are an effective method for discriminating between culturing regimens. Genotype 5 is known to be more recalcitrant towards germination than genotype 7.

EXAMPLE 3

Determination of Biochemical Maturity in Loblolly Pine Somatic Embryos

Embryos from two genotypes of loblolly pine were cultured as described earlier. Samples of embryos that appeared to be morphologically mature were harvested from the Stage III embryo development medium approximately 12 and 15 weeks after plating the early stage embryo culture. Replicate samples were taken from different culture plates and 10 embryos from each culture were pooled. The embyos were treated and prepared for HPLC analysis as described for the seed embryos. Sugar alcohol levels were as found in Table 7 which follows.

TABLE 7

Sugar Alcohols in Loblolly Pine Somatic Embryos

| Culture Time, weeks | 12 | 15 |
|---|---|---|
| Pinitol, nM/embryo | Negligible | Negligible |
| Myo-inositol, nM/embryo | 58.2 | —* |
| D-chiro-inositol, nM/embryo | 23.5 | 50.5 |
| Fagopyritol B1, nM/embryo | Negligible | Negligible |

*Sample contaminated

Considerable difference is seen between this sample of somatic embryos and the zygotic embryos of Example 1 in the content and distribution of the sugar alcohols. The additional three weeks on the medium increased D-chiro-inositol but no pinitol or fagopyritol B1 was present in either sample.

Embryos of the same genotype as above were cultured for 12 weeks in similar manner to those just described. However, they were then lifted from the development medium on their filter paper support and placed in a closed dish over saturated K$_2$SO$_4$ solution for three weeks. At room temperature this created a 97% relative humidity environment and resulted in slow, partial desiccation of the embryos. This treatment has been found from experience to be almost essential for ensuring good germination. Again, sugar alcohols present were determined by HPLC analysis with the following results seen in Table 8.

TABLE 8

Sugar Alcohols in Partially Desiccated Somatic Embryos

| Sample No. | 1 | 2 |
|---|---|---|
| D-chiro-inositol, nM/embryo | 32.6 | 39.9 |
| D-chiro-inositol, nM/mg dry weight | 74.1 | 90.7 |
| Fagopyritol B1, nM/embryo | 2.8 | 4.1 |
| Fagopyritol B1, nM/mg dry weight | 6.4 | 9.3 |

While levels of fagopyritol B1 did not reach those present in mature zygotic embryos, it is important that it did appear during the partial desiccation. Since the partial desiccation appears necessary for good germination, it may be regarded as a good indication that the presence of fagopyritol B1 loblolly pine somatic embryos is also essential.

It will be evident to those skilled in the art that many variations of the present invention not described in the examples can be made without departing from the spirit of the invention. Thus, the invention should be regarded as limited only as it is defined in the appended claims.

BIBLIOGRAPHY

Attree, S. M. and L. C. Fowke 1995 Desiccated conifer somatic embryos. U.S. Pat. No. 5,464,769.

Baron, Frank J. 1970 Metabolic patterns in dormant and germinating seeds of sugar pine (*Pinus lambertiana*, Dougl.). In *Advancing Frontiers of Plant Sciences*, Lokesh Chandra ed., 24: 47–63.

Bernabé, M., R. Fenwick, J. Frias, J. Jiménez-Barbero, K. Price, S. Valverde, and C. Vidal-Valverde 1993 Determination, by NMR spectroscopy, of the structure of ciceritol, a pseudotrisaccharide isolated from lentils. *Journal of Agricultural and Food Chemistry* 41: 870–872.

Chien, C. -T., T. -P. Lin, C. -G. Jou, and G. -R. Her 1996 Occurrence of a novel galactopinitol and its changes with other non-reducing sugars during development of *Leucaena leucocephala* seeds. *Plant Cell Physiology* 37: 539–544.

Górecki, R. J., A. I. Piotrowicz-Cieslak, L. B. Lahuta, and R. L. Obendorf 1997 Soluble carbohydrates in desiccation tolerance of yellow lupin seeds during maturation and germination. *Seed Science Research* 7: 107–115.

Gupta, P. K. and D. J. Durzan 1987 Biotechnology of somatic polyembryogenesis and plantlet regeneration in loblolly pine. Bio/Technology 5:147–151.

Gupta, P. K. and G. S. Pullman 1991 Method for reproducing coniferous plants by somatic embryogenesis using abscisic acid and osmotic potential variation. U.S. Pat. No. 5,036,007.

Handley, L. W., L. W. Pharr, and R. F. McFeeters 1983 Relationship between galactinol synthase activity and sugar compositions of leaves and seeds of several crop species. *Journal of the American Society of Horticultural Science* 108(4): 600–605.

Horbowicz, M., P. Brenac, and R. L. Obendorf 1998 Fagopyritol B1, O-α-D-galactopyranosyl-(1→2)-D-chiro-inositol, a galactosyl cyclitol in maturing buckwheat seeds associated with desiccation tolerance. *Planta* 205: 1–11.

Horbowicz, M. and R. L. Obendorf 1994 Seed desiccation tolerance and storability: Dependence on flatulence-producing oligosaccharides and cyclitols-review and survey. *Seed Science Research* 4: 385–405.

Horbowicz, M., R. L. Obendorf, B. D. McKersie, and D. R. Viands 1995 Soluble saccharides and cyclitols in alfalfa (*Medicago sativa* L.) somatic embryos, leaflets, and mature seeds. *Plant Science* 109: 191–198.

Kuo, T. M. 1992 Isolation and identification of galactinol from castor oilseed meal. *Journal of the American Oil Chemists Society* 69: 569–574.

Kuo, T. M., C. A. Lowell, and T. C. Nelsen 1997 Occurrence of pinitol in developing soybean seed tissues. *Phytochemistry* 45: 29–35.

Murphy, J. B. and M. F. Hammer 1988 Respiration and soluble sugar metabolism in sugar pine embryos. *Physiologia Plantarum* 74: 95–100.

Obendorf, R. L. 1997 Oligosaccharides and galactosyl cyclitols in seed desiccation tolerance (Review Update). *Seed Science Research* 7: 63–74.

Obendorf, R. L., M. Horbowicz, A. M. Dickerman, P. Brenac, and M. E. Smith 1998 Soluble oligosaccharides and galactosyl cyclitols in maturing soybean seeds In planta and In vitro. *Crop Science* 38: 78–84.

Peterbauer, T. and A. Richter 1998 Galactosylononitol and stachyose synthesis in seeds of adzuki bean. *Plant Physiology* 117: 165–172.

Phillippy, Brian Q. 1998 Identification of inositol 1,3,4-trisphosphate 5-kinase and inositol 1,3,4,5-tetrakisphosphate 6-kinase in immature soybean seeds. *Plant Physiology* 116: 291–297.

Teasdale, R. D., P. A. Dawson, and H. W. Woolhouse 1986 Mineral nutrient requirements of loblolly pine. (Pinus taeda cell suspension culture). *Plant Physiology* 82: 942–945.

What is claimed is:

1. A method of determining the maturity of southern pine embryos which comprises:

determining the content of sugar alcohols in the embryos, said alcohols including at least D-chiro-inositol, and fagopyritol B1; and noting the time in embryo development when the content of D-chiro-inositol begins to decrease and fagopyritol has appeared, at which time the embryos are approaching biochemical maturity and readiness for harvest.

2. The method of claim 1 in which the embryos are zygotic embryos in natural seeds and the sugar alcohol content and composition is used as an indicator of optimum cone harvest time.

3. The method of claim 2 in which cone harvest is delayed until the content of fagopyritol exceeds that of D-chiro-inositol.

4. The method of claim 1 in which the embryos are somatic embryos produced by tissue culture and the sugar alcohol content and composition is used as an indicator of readiness for germination.

5. The method of claim 1 in which the sugar alcohol content is determined by high pressure liquid chromatography using anion exchange techniques.

* * * * *